United States Patent
Kalinin et al.

(10) Patent No.: US 9,418,138 B2
(45) Date of Patent: Aug. 16, 2016

(54) METHOD AND SYSTEM FOR DETERMINING SETS OF VARIANT ITEMS

(71) Applicant: Amazon Technologies, Inc., Seattle, WA (US)

(72) Inventors: Alexander Y. Kalinin, Seattle, WA (US); Amber Roy Chowdhury, Bellevue, WA (US); Vijay Kumar, Seattle, WA (US)

(73) Assignee: Amazon Technologies, Inc., Reno, NV (US)

( * ) Notice: Subject to any disclaimer, the term of this patent is extended or adjusted under 35 U.S.C. 154(b) by 0 days.

(21) Appl. No.: 14/850,934

(22) Filed: Sep. 10, 2015

(65) Prior Publication Data
US 2015/0379117 A1    Dec. 31, 2015

Related U.S. Application Data

(63) Continuation of application No. 12/341,003, filed on Dec. 22, 2008, now Pat. No. 9,135,396.

(51) Int. Cl.
*G06F 17/30* (2006.01)
*G06F 19/24* (2011.01)
*G06F 19/18* (2011.01)
*G06F 19/28* (2011.01)

(52) U.S. Cl.
CPC .... *G06F 17/30598* (2013.01); *G06F 17/30321* (2013.01); *G06F 17/30345* (2013.01); *G06F 17/30958* (2013.01); *G06F 19/18* (2013.01); *G06F 19/24* (2013.01); *G06F 19/28* (2013.01)

(58) Field of Classification Search
CPC .......... G06F 17/30598; G06F 17/30345; G06F 17/30958; G06F 17/30321; G06F 17/2211; G06F 19/24
USPC ............................................... 707/749
See application file for complete search history.

(56) References Cited

U.S. PATENT DOCUMENTS

| | | | |
|---|---|---|---|
| 5,577,249 A | 11/1996 | Califano | |
| 5,873,082 A | 2/1999 | Noguchi | |
| 5,978,797 A | 11/1999 | Yianilos | |
| 6,556,991 B1 * | 4/2003 | Borkovsky | G06F 17/30696 707/737 |
| 6,618,727 B1 | 9/2003 | Wheeler et al. | |
| 6,636,849 B1 | 10/2003 | Tang et al. | |
| 6,785,672 B1 | 8/2004 | Floratos et al. | |
| 7,020,651 B2 | 3/2006 | Ripley | |

(Continued)

*Primary Examiner* — Jean B Fleurantin
*Assistant Examiner* — Evan Aspinwall
(74) *Attorney, Agent, or Firm* — Robert C. Kowert; Meyertons, Hood, Kivlin, Kowert & Goetzel, P.C.

(57) ABSTRACT

Various embodiments of a method and system for determining sets of variant items are described. Various embodiments may include a system configured to generate multiple item pairs each corresponding to a particular item and another item determined to be similar to the particular item. For the particular item and the other item, each item pair may include a respective sequence of text strings (e.g., a title). For each item pair, the system may perform a corresponding text alignment and determine one or more misalignments of the item pair. The system may also assign a similarity score to each item pair; the similarity score may be dependent on the misalignment(s) determined for the particular item pair. Based on each aligned item pair and the similarity score assigned to that aligned item pair, the system may generate an indication specifying that each of a set of items are variants of each other.

20 Claims, 9 Drawing Sheets

(56) References Cited

U.S. PATENT DOCUMENTS

| | | |
|---|---|---|
| 7,082,426 B2 | 7/2006 | Musgrove et al. |
| 7,548,652 B1 | 6/2009 | Ahrens |
| 7,664,735 B2 | 2/2010 | Zhang et al. |
| 7,702,631 B1 * | 4/2010 | Basu ................ G06F 17/30489 707/999.006 |
| 7,818,278 B2 | 10/2010 | Padovitz et al. |
| 7,882,119 B2 | 2/2011 | Bergholz et al. |
| 7,970,773 B1 | 6/2011 | Thirumalai et al. |
| 8,266,173 B1 | 9/2012 | Reztlaff, II et al. |
| 8,285,719 B1 | 10/2012 | Long et al. |
| 8,606,690 B2 | 12/2013 | Singer |
| 2003/0200198 A1 | 10/2003 | Chandrasekar et al. |
| 2004/0260694 A1 | 12/2004 | Chaudhuri et al. |
| 2006/0004857 A1 | 1/2006 | Daniel et al. |
| 2006/0059173 A1 | 3/2006 | Hirsch et al. |
| 2006/0274062 A1 | 12/2006 | Zhang et al. |
| 2007/0239694 A1 | 10/2007 | Singh et al. |
| 2008/0120292 A1 | 5/2008 | Sundaresan et al. |
| 2008/0313111 A1 | 12/2008 | Padovitz et al. |
| 2008/0313165 A1 * | 12/2008 | Wu ..................... G06Q 10/101 |
| 2009/0138380 A1 | 5/2009 | Roseman et al. |
| 2009/0171955 A1 | 7/2009 | Merz et al. |
| 2009/0182728 A1 | 7/2009 | Anderson |
| 2009/0216689 A1 | 8/2009 | Zelenko |
| 2009/0234869 A1 | 9/2009 | Azvine et al. |
| 2009/0271363 A1 | 10/2009 | Bayliss |
| 2009/0319518 A1 | 12/2009 | Koudas et al. |
| 2010/0106724 A1 | 4/2010 | Anderson |
| 2013/0138688 A1 | 5/2013 | Anderson |

* cited by examiner

METHOD AND SYSTEM FOR DETERMINING SETS OF VARIANT ITEMS

This application is a continuation of U.S. patent application Ser. No. 12/341,003, filed Dec. 22, 2008, which is hereby incorporated by reference in its entirety.

BACKGROUND

The Internet, sometimes called simply "the Net," is a worldwide system of computer networks in which a client at any one computer may, with permission, obtain information from any other computer. The most widely used part of the Internet is the World Wide Web, often abbreviated "WWW," which is commonly referred to as "the web." The web may be defined as all the resources (e.g., web pages and web sites) and users on the Internet that use the Hypertext Transfer Protocol (HTTP) or variations thereof to access the resources. A web site is a related collection of web files that includes a beginning file called a home page. From the home page, the user may navigate to other web pages on the web site. A web server program is a program that, using the client/server model and HTTP, serves the files that form the web pages of a web site to the web users, whose computers contain HTTP client programs (e.g., web browsers) that forward requests and display responses. A web server program may host one or more web sites.

Various applications of the Internet, and of the web, involve marketplaces that provide goods and/or services for sale. For instance, consumers may visit a merchant's website to view and/or purchase goods and services offered for sale by the merchant (and/or third party merchants). Some network-based marketplaces (e.g., Internet- or web-based marketplaces) include large electronic catalogues of items offered for sale. For each item offered for sale, such electronic catalogues typically include product detail pages (e.g., a web page) that specifies various information about the item, such as a description of the item, one or more pictures of the item, as well as specifications (e.g., weight, dimensions, capabilities) of the item. In some cases, merchants (e.g., suppliers of products offered for sale via the network-based marketplace) may provide data from which such product detail pages may be generated. In some cases, the data provided by a merchant may be organized in a structured fashion. For instance, the data provided by the merchant may include a list of attributes (e.g., weight, dimensions, color, model number, and other attributes) as well as values for such attributes. In other cases, the data provided by a merchant may be relatively unstructured. For instance, such data may be an unformatted text description of the item.

Figure 1:
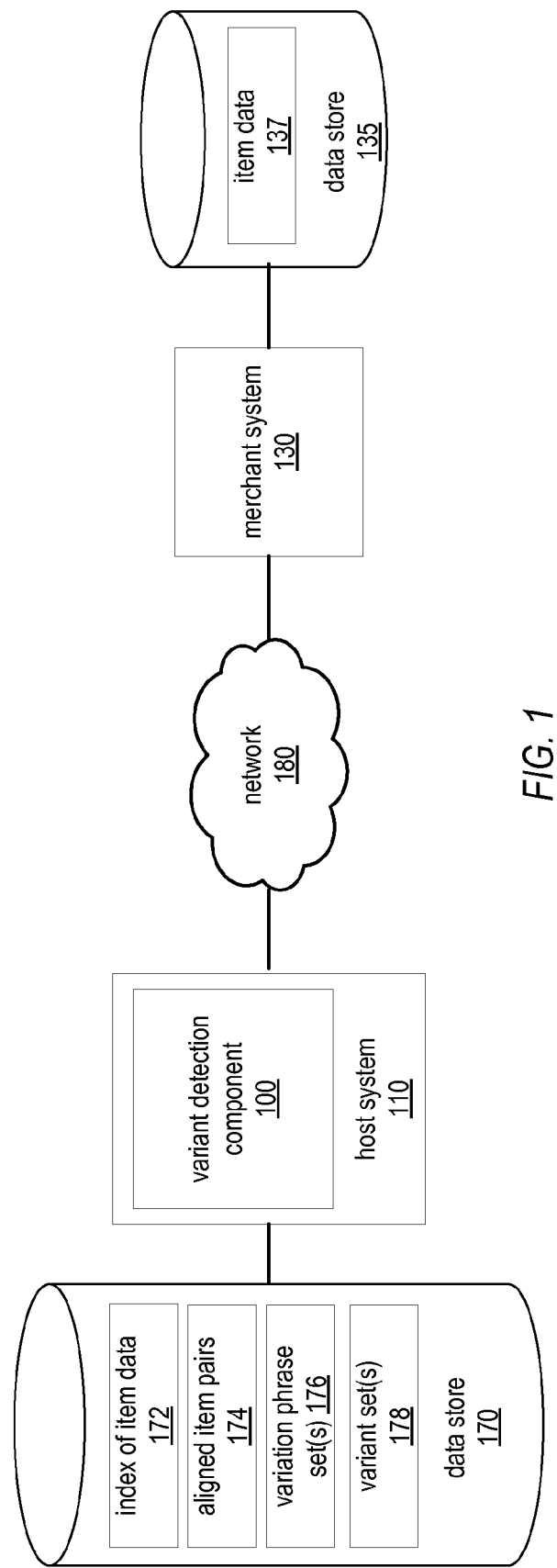
FIG. 1 illustrates a block diagram of a system including a variant detection component, according to some embodiments.

While the method and system for determining sets of variant items is described herein by way of example for several embodiments and illustrative drawings, those skilled in the art will recognize that the method and system for determining sets of variant items is not limited to the embodiments or drawings described. It should be understood, that the drawings and detailed description thereto are not intended to limit the method and system for determining sets of variant items to the particular form disclosed, but on the contrary, the intention is to cover all modifications, equivalents and alternatives falling within the spirit and scope of the method and system for determining sets of variant items as defined by the appended claims. The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include," "including," and "includes" mean including, but not limited to.

Detailed Description Of Embodiments

Introduction

Various embodiments of a method and system for determining sets of variant items are described. The method and system for determining sets of variant items may include a variant detection component, according to some embodiments. The variant detection component may be configured to receive item data for multiple items and determine one or more sets of items from the multiple items. Each of such sets may be a variant set, which may include variant items. In some embodiments, each item of such set may be a variant item (or "variant") of the same item and/or a variant of each other item of the set. In some embodiments, variants may differ by only one or more variant attributes, examples of which may include color and size. Other examples of variant attributes are described in more detail below. The received item data may include item titles, item descriptions, item specifications, and other information about items. In various embodiments, the item data may for a given item include a sequence of text strings, which may in some cases be descriptive of the item. Such item data may be used for a variety of purposes including the generation of product detail pages (e.g., web pages offering the items for sale). In various embodiments, a given text string may include, but is not limited to, one or more characters, numbers or symbols and/or one or more strings (e.g., groups) of one or more characters, numbers or symbols.

From the item data, the variant detection component may be configured to determine, for a particular item for which item data is received, one or more similar item(s) for which item data is received. In some cases, some of the similar item(s) may be variants of the particular item whereas other ones of the similar item(s) may be similar to the particular item but not necessarily a variant of the particular item. The variant detection component may be configured to evaluate multiple item pairs, each item pair corresponding to a particular item (e.g., an item under evaluation) and a respective item determined to be similar to that particular item, such as described above. Each item pair may include a sequence of text strings received for the particular item and a sequence of text strings received for the similar item (e.g., the other item) of that item pair. Accordingly, for a particular item, the variant detection component may be configured to generate one or more item pairs each corresponding to that item and a different item of multiple items determined to be similar to the particular item.

For each item pair, the variant detection component may be configured to align the item pair. Aligning the item pair may include performing a text alignment on the two sequences of text strings that are included in the item pair. One example of performing text alignment may include performing a text alignment algorithm or technique on the two sequences of text strings included within the item pair. One example of such a text alignment algorithm or technique may include a version of the Needleman-Wunsch text alignment algorithm. However, in other embodiments any other text alignment algorithm or technique configured to align two sequences of text strings with respect to each other may be employed, whether such techniques are presently known or developed in the future. In some cases, the variant detection component may align a given item pair by transforming that item pair into an aligned item pair. In other cases, the variant detection component may align a given item pair by generating a new aligned item pair that corresponds to the original unaligned item pair.

For each aligned item pair, the variant detection component may be configured to assign the aligned item pair a similarity score, which may in some cases indicate a degree of confidence that the two items corresponding to that item pair are variants of each other. In some cases, the score may indicate a degree of the likelihood or probability that the two items corresponding to that item pair are variants of each other. In various embodiments the score assigned to a given aligned item pair may be generated from one or more subscores (e.g., the assigned score may be a sum of the subscores). In various embodiments, the variant detection component may be configured to determine a misalignment in an aligned item pair, and generate a subscore dependent upon that misalignment.

In the manner described above, the variant detection component may be configured to, generate sets of aligned item pairs for each of multiple items. The variant detection component may be configured to generate a representation of an affinity graph comprising multiple nodes; each of such nodes may be coupled to one or more other nodes by a respective edge. In various embodiments, each node of the affinity graph may correspond to an item for which an aligned item pair was generated. Each edge between a given node (corresponding to a particular item of an aligned item pair) and another node (corresponding to the other item of that aligned item pair) may be weighted according to an assigned score (e.g., the score assigned to that aligned item pair). The variant detection component may be configured to determine a variant set of items by determining a cluster of nodes of the affinity graph and, for each node of that cluster, indicating the corresponding item as being a member of the variant set. In various embodiments, the variant detection component may be configured to perform a graph clustering algorithm to determine the aforesaid cluster of nodes.

Each variant set determined by the variant detection component may be utilized for a variety of purposes. In one embodiment, a variant set may be utilized to consolidate search results by presenting only a single search result for a given variant set (e.g., a "parent" search result). The other search results of that variant set (e.g., "child" search results) may be hidden from view in the list of search results. In other cases, multiple product detail pages may be collapsed into a single product detail page (e.g., for a "parent" item) from which one or more variant attributes may be selected in order to select a particular item of the variant set (a "child" item).

Variant Detection Component

FIG. 1 illustrates a system including a variant detection component 100, as described herein. In various embodiments, the illustrated variant detection component 100 may be configured to receive via one or more networks (e.g., network 180) item data 137 retrieved from a data store 135 controlled by a merchant system 130. Network 180 may include a Local Area Network (LAN) (e.g., an Ethernet or Corporate network), a Wide Area Network (WAN) (e.g., the Internet), some other network configured to transport data, and/or some combination thereof. In some embodiments, merchant system 130 may be controlled by a merchant that provides items to be sold by a distributor that controls host system 110. In some cases, merchant system 130 may be configured to, for each of one or more items, provide a corresponding portion of item data 137 to the variant detection component 100. The received item data 137 may include item titles, item descriptions, item specifications, and other information about items. In various embodiments, item data 137 may for a given item include a sequence of text strings, which may in some cases be descriptive of the item. Item data 137 may be unstructured information, which may in some cases include information that is not structured according to particular item attributes (e.g., color, size, weight, dimensions, etc.). For instance, in one embodiment, unstructured information may include data representing one or more unformatted text strings. While in some embodiments the unstructured information may include such attributes as text strings, note that such information is not specified as an attribute (or attribute-value pair) within the unstructured information. One example of item data may include a sequence of text strings, such as "Size 5 Blue Basketball Jersey Adult," which may represent an item title. Note that the item data described herein is not limited to title and may include any sequence of text strings, such as text strings representing a product description or product specifications. Also note that each text string of a sequence of text strings may include one or more characters, numbers, or symbols. For instance, in the previous example, the text strings include "Size", "5", "Blue", "Basketball", "Jersey" and "Adult." In this particular example, each text string in the sequence is delimited by white space; however, in other cases other delimiters (e.g., commas, semicolons, etc.) may be utilized. In some embodiments, the variant detection component may evaluate text strings as words or as phrases (multiple words). For instance, in the above example, the variant detection component may evaluate "Size" and "5" separately (e.g., as separate words) or together as "Size 5" (e.g., as a phrase).

Variant detection component 100 may be configured to store received item data 137 within data store 170. As is the case in the illustrated embodiment, variant detection component 100 may be configured to store item data 137 as searchable index of item data 172. In various embodiments, variant detection component 100 may be configured to query search index 172 with a request including item data for a particular item and receive one or more similar items as a response to the request. Each of the one or more similar items may be items corresponding to item data that is similar to the item data corresponding to the item for which the index was queried. In some embodiments, the variant detection component 100 may be configured to apply a threshold to such search results to remove search results that are not highly relevant to the search query. In other embodiments, the variant detection component may be configured to utilize other techniques to determine, for a particular item for which item data is received, one or more similar item(s) for which item data is received. Such techniques may in some embodiments include utilizing one or more text comparison algorithms (e.g., a version of the cosine similarity or Jaccard algorithms) to determine, for a given item, one or more other items corresponding to item data that is similar to item data of the given item. As is the case for searching the index of item data, the variant detection component may be configured to apply a threshold to the results of the text comparison techniques in order to remove results that are not highly relevant.

For each item for which item data is received, variant detection component 100 may be configured to generate aligned item pairs, such as aligned item pairs 174 stored in data store 170. To generate one or more aligned item pairs for a particular item, the variation detection component may determine one or more similar items associated with item data that is determined to be similar to the item data of the particular item. For instance, in an embodiment where each item's item data is an item title, variant detection component 100 may determine one or more items having item titles that are similar to the item title of the given item. The one or more items having item titles that are similar to the item title of the given item may be determined through any of the techniques described above (e.g., searching the index of item data or performing a text comparison technique). For each item determined to correspond to item data that is similar to the item data of the particular item, the variant detection component may be configured to generate a respective item pair; each item pair may include a sequence of text strings from the item data received for the particular item and a sequence of text strings from the item data received for a respective similar item. Accordingly, for a particular item, the variant detection component may be configured to generate one or more item pairs each corresponding to that item and a different item of multiple items determined to be similar to the particular item.

For each item pair generated, variant detection component 100 may be configured to align the item pair. To align the item pair, variant detection component 100 may be configured to perform text alignment on the two sequences of text strings that are included in the item pair (e.g., one sequence for each of the two items to which the item pair corresponds). One example of performing text alignment may include performing a text alignment algorithm on the two sequences of text strings included within the item pair. One example of such a text alignment algorithm may include a version of the Needleman-Wunsch algorithm. However, in other embodiments any other text alignment technique for aligning two sequences of text strings with respect to each other may be employed, whether such text alignment algorithm is presently known or developed in the future.

For each aligned item pair, variant detection component 100 may be configured to assign the aligned item pair a score, which may in some cases indicate a degree of confidence that the two items corresponding to that item pair are variants of each other. In some cases, the score may indicate a degree of the likelihood or probability that the two items corresponding to that item pair are variants of each other. In various embodiments the score assigned to a given aligned item pair may be generated from one or more subscores (e.g., the assigned score may be a sum of the subscores). In various embodiments, variant detection component 100 may be configured to determine a misalignment in an aligned item pair, and generate a respective subscore dependent upon that misalignment. To determine a misalignment in an item pair corresponding to a particular item and another item, variation detection component 100 may be configured to evaluate corresponding pairs of text strings from each of the two sequences of text strings corresponding to the particular item and the other item. In some embodiments, variation detection component 100 may determine that a misalignment exists between the two sequences in response to determining that a pair of text strings from the two sequences are mismatched. For instance, in one embodiment, the pair of text strings may include the text string "yellow" from one of the text sequences and the term "red" from the other text sequence. Since such text strings do not match (i.e., the text strings are not the same), variation detection component 100 may determine that a mismatch has been detected. Based on the nature of the mismatch, variant detection component 100 may be configured to assign a subscore to the mismatch. As described above, all subscores for a given aligned item pair may be summed, and the result of that summation may be assigned to the aligned item pair as a similarity score.

In the manner described above, variant detection component 100 may be configured to generate sets of aligned item pairs 174 for each of multiple items. The variant detection component may be configured to generate a representation of an affinity graph comprising multiple nodes; each of such nodes may be coupled to one or more other nodes by a respective edge. In various embodiments, each node of the affinity graph may correspond to an item for which an aligned item pair was generated. Each edge between a given node (corresponding to a particular item of an aligned item pair) and another node (corresponding to the other item of that aligned item pair) may be weighted according to an assigned score (e.g., the similarity score assigned to that aligned item pair). The variant detection component may be configured to determine a variant set of items by determining a cluster of nodes of the affinity graph and, for each node of that cluster, indicating the corresponding item as being a member of the variant set. In various embodiments, the variant detection component may be configured to perform a graph clustering algorithm or technique to determine the aforesaid cluster of nodes. In some embodiments, some edges (corresponding to assigned similarity scores) may be omitted from the above analysis. For instance, in one embodiment, variant detection component 100 may be configured to omit edges that do not meet a threshold (i.e., the similarity score of the edge does not meet a threshold specifying a minimum similarity score).

Figure 2:
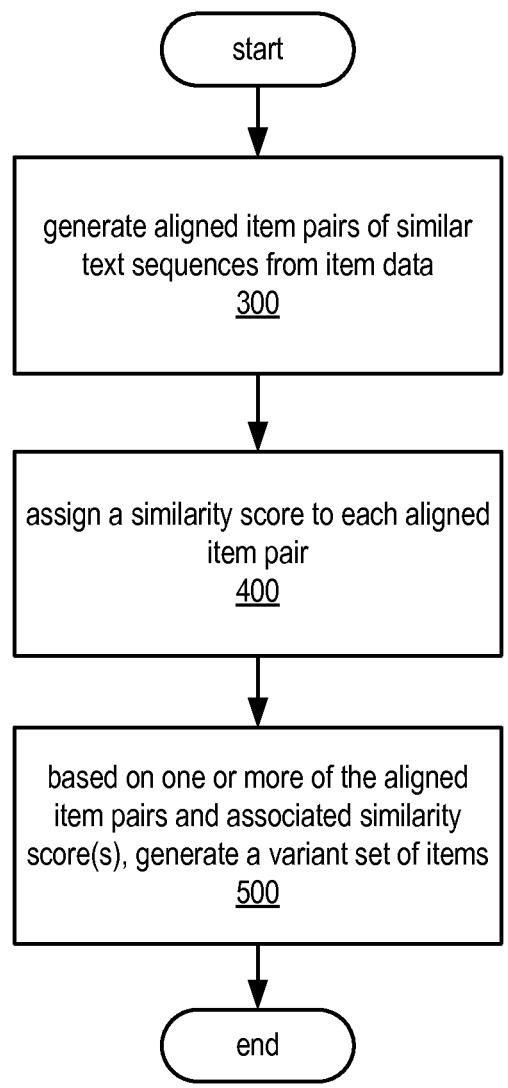
FIG. 2 illustrates a flowchart of an example method for determining one or more variant sets of items from item data, according to some embodiments.

Methods for Determining One or More Variant Sets of Items from Unstructured Data FIG. 2 illustrates one example of a high-level method for determining one or more variant sets of items from item data that does not specify variant attributes (such data may be referred to herein as "unstructured data"). Each block of the illustrated flow chart represents a high-level representation of the flowcharts illustrated with respect to FIG. 3-5, as described in more detail herein. In various embodiments, each of the illustrated methods may be performed by the variant detection component described herein. As illustrated by block 300, the method may include generating aligned pairs of similar text sequences from item data, which may include the aforesaid unstructured data. For instance, in some embodiments, such item data may be data received from a merchant that supplies one or more items for sale by a distributor. In various embodiments, the item data evaluated may be received from a single merchant; however, in some embodiments the item data may be received from multiple different merchants. The unstructured data may include item titles, item descriptions, item specifications, and other unstructured information about respective items. In various embodiments, the item data may include a sequence of text strings for a given item, which may in some cases be descriptive of the item. For a given item being evaluated, the method may include determining one or more similar items that correspond to the item data (e.g., sequence of text strings) that is similar to item data of the given item. The method may further include generating multiple item pairs that each include item data (e.g. a sequence of text strings) of the given item being evaluated and item data of a different one of the one or more similar items. The method may further include, on a pair-wise basis, performing text alignment on each of the generated item pairs to generate multiple aligned item pairs.

As illustrated by block 400, the method may include assigning a similarity score to each of such aligned item pairs. For example, in one embodiment, the method may include determining one or more mismatches between the sequences of text strings of the item pairs, and assigning similarity scores to the aligned item pairs based on the mismatches. As illustrated by block 500, the method may include, based on one or more of the aligned item pairs and each pair's associated similarity score, generating a variant set of items. In various embodiments, the items of the variant set of items are each variants of each other. In some embodiments, the method may include generating a graph based on the aligned item pairs and associated similarity scores, and performing graph clustering to determine a cluster of items. In some embodiments, a determined cluster of items may be equivalent to a variant set of items.

Figure 3:
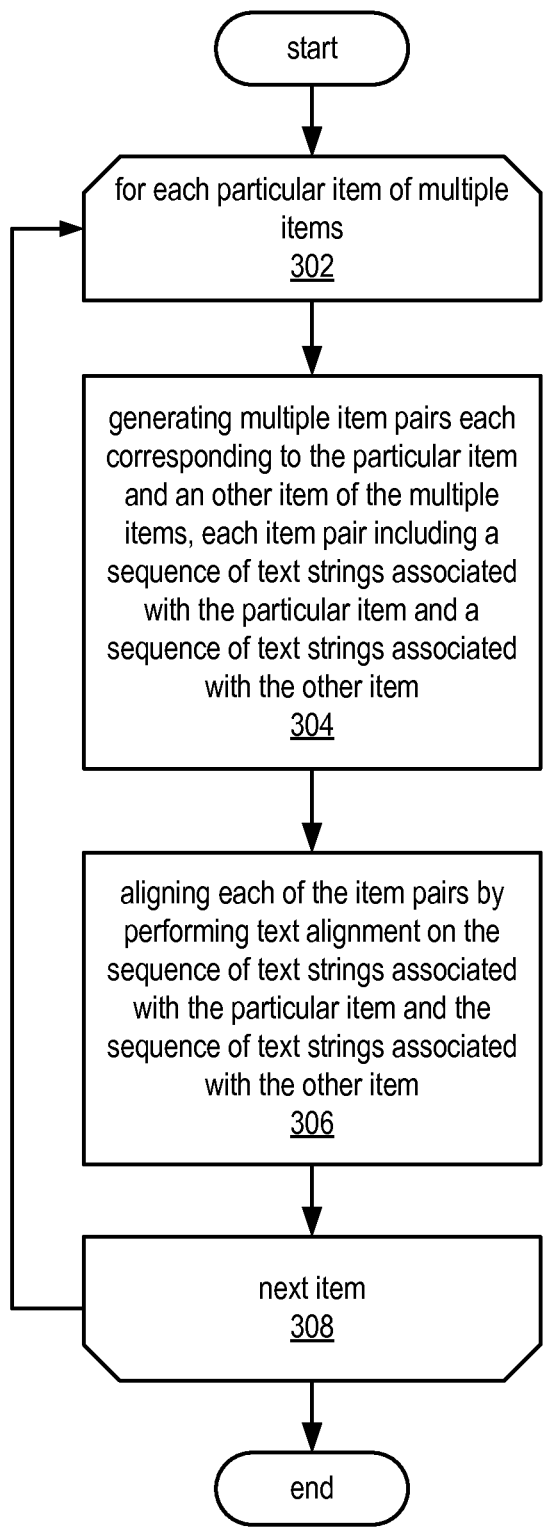
FIG. 3 illustrates a flowchart of an example method for generating aligned item pairs from item data, according to some embodiments.

FIG. 3 illustrates a flowchart of one example of a method for generating item pairs from item data (e.g., sequences of text pairs) of multiple items. Note that the illustrated method may be performed on an item by item basis. Accordingly, the method may in some cases be performed when new item data is received for a particular item. In various embodiments, the illustrated method may be performed by variant detection component 100 described above. As illustrated by block 302 and 308, the illustrated method may be performed for multiple items, such as items for which item data has been received (e.g., from a merchant). As illustrated by block 304, the method may include generating multiple item pairs that each correspond to the current item and another item of the multiple items. In various embodiments, the other item may be an item that is determined to be similar to the current item. For instance, the method may include searching an index of items and corresponding item data (e.g., index 172 described above) to determine one or more items that are similar to the current item. Each item pair may include two sequences of text strings, one sequence of text strings associated with the current item and another sequence of text strings associated with the other item of the item pair.

Figure 6:
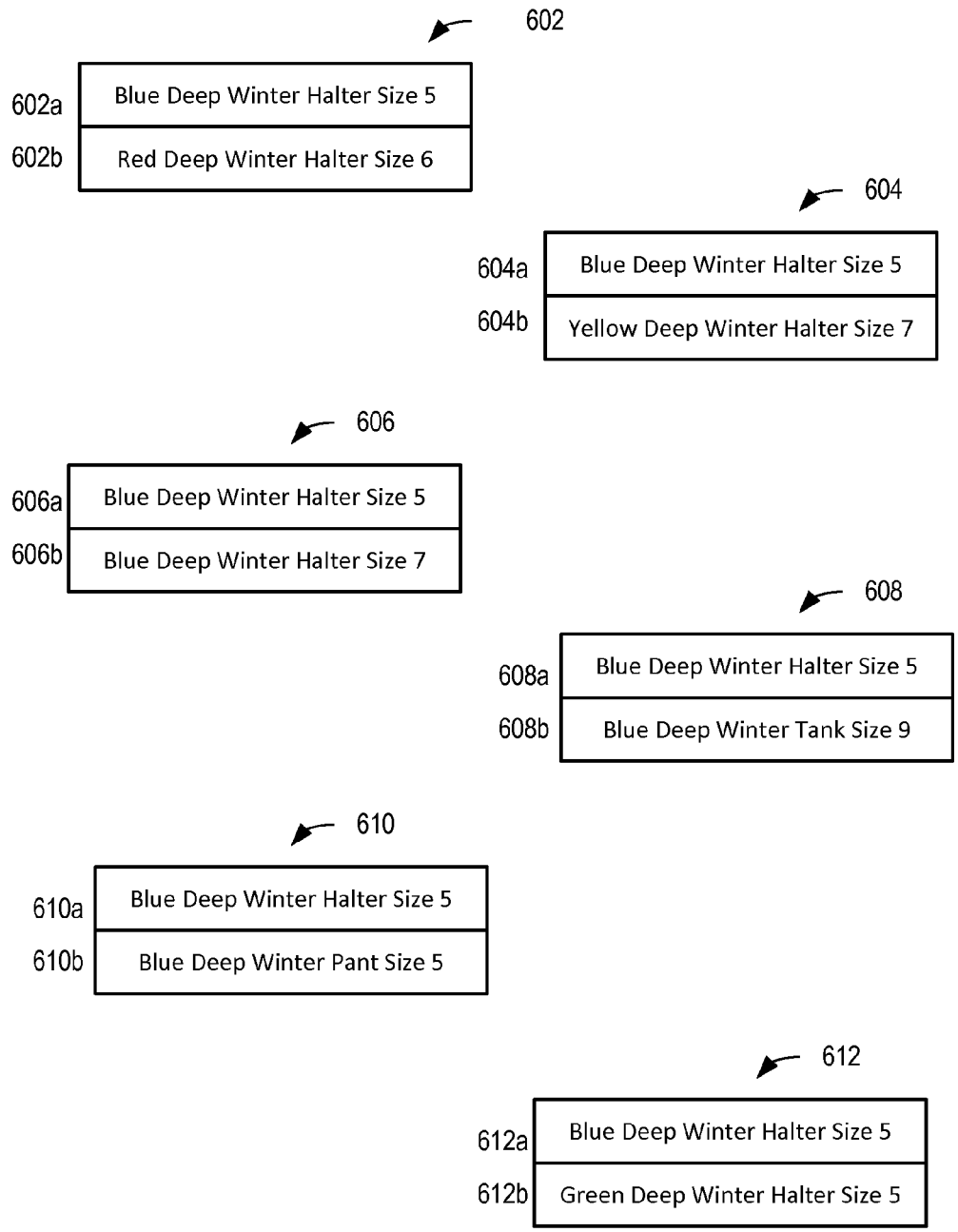
FIG. 6 illustrates examples of aligned item pairs, according to some embodiments.

As indicated by block 306, the method may further include aligning each of the generated item pairs. For a given item pair, generating an aligned item pair may include performing text alignment on both sequences of text strings of the item pair. In one embodiment, performing text alignment on the item pair may include performing a text alignment algorithm or technique on the item pair, one example of which may include a version of the Needleman-Wunsch algorithm. In other embodiments, the method may include performing text alignment by performing any other text alignment algorithm or technique configured to align two sequences of text strings with respect to each other, whether such text alignment algorithm or technique is presently known or developed in the future. In one particular embodiment, the method may include performing a particular version of the Needleman-Wunsch algorithm. In one embodiment, the Needleman-Wunsch algorithm may include an implementation that penalizes gaps in sequences of text strings more than a mismatch between two text strings of each sequence. In this manner, gaps that exist in the unaligned item pairs may no longer be present in the item pairs aligned according to this particular version of the Needleman-Wunsch algorithm. Some examples of gapless aligned item pairs are illustrated in FIG. 6, which is described in more detail below. Note that the item pairs illustrated in Figure may be generated according to any of the methods described herein including methods that do not include a version of the Needleman-Wunsch algorithm. Also note that the term aligned item pair may be used herein to refer to an item pair upon which text alignment has been performed. Such text alignment may in various embodiments be performed in a "best fit" manner; accordingly, one or more misalignments (e.g., mismatched words) may still exist within an "aligned item pair."

Referring collectively to FIG. 3 and FIG. 6, examples of aligned item pairs are illustrated. Such aligned item pairs may be generated by the example method of FIG. 3, according to some embodiments. Aligned item pairs 602-612 each include corresponding aligned item data 602a, 602b, 604a, 604b and so on, as illustrated. In the illustrated embodiment, each aligned item pair may correspond to the result of one pass (e.g., blocks 304-306) of the illustrated method of FIG. 3. For instance, as illustrated "Blue Deep Winter Halter Size 5" (which is illustrated as a component of each of the aligned item pairs 602-612) may represent the item data for the current item (see e.g., block 302) of one pass of the method illustrated by FIG. 3. In various embodiments, multiple sets of aligned item pairs, such as those illustrated, may be generated for each of multiple items (e.g., as the illustrated method is performed multiple times).

Figure 4:
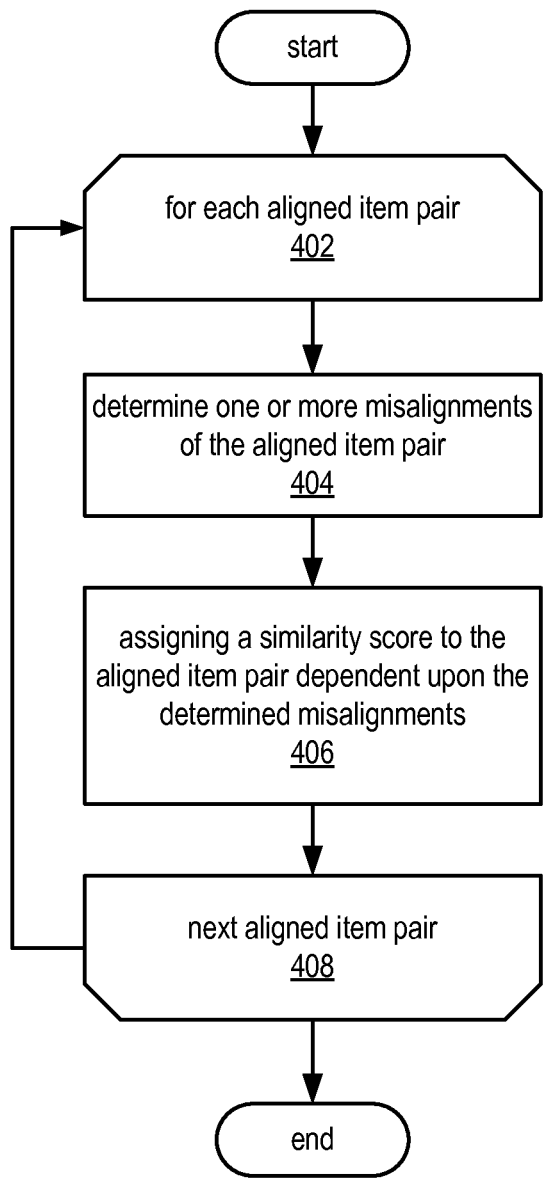
FIG. 4 illustrates a flowchart of an example method for assigning similarity scores to aligned item pairs, according to some embodiments.

For each of the aligned item pairs, the method may include assigning similarity scores to each of the aligned item pairs. FIG. 4 illustrates a flowchart of one example of a method for assigning similarity scores to each aligned item pair. In various embodiments, the illustrated method of FIG. 4 may be performed by the variant detection component described herein. As illustrated by block 402 and 408, the illustrated method may be performed for each of multiple aligned item pairs (e.g., aligned item pairs 602-612). As illustrated by block 404, the method may include determining one or more misalignments of the current aligned item pair. In various embodiments, determining one or more misalignments may include determining whether each corresponding word (or phrase) of an aligned item pair matches each other. If corresponding words (or phrases) match, the method may include determining that such words are in alignment. If corresponding words (or phrases) do not match, the method may include determining that such words are misaligned.

Figure 7:
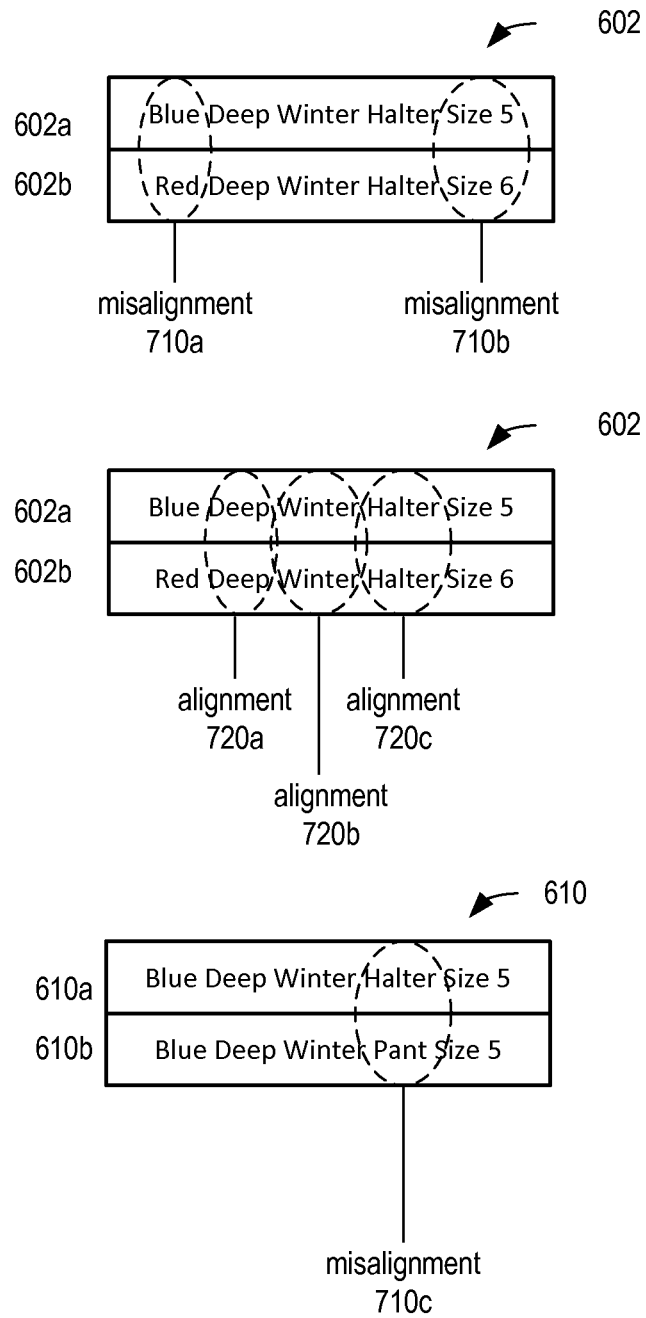
FIG. 7 illustrates examples of alignments and misalignments in an example aligned item pair, according to some embodiments.

Referring collectively to FIG. 4 and FIG. 7, aligned item pairs 602 and 610 are illustrated. FIG. 7 illustrates the evaluation of an aligned item pair on a word-pair (or phrase-pair) basis. In other words, each word (or phrase) of one sequence of text strings (e.g., sequence 602a) is compared on a word-by-word basis with the corresponding word of the other sequence of text strings (e.g., sequence 602b). For instance, the first word (or phrase) of each sequence may be compared determine whether such words match, the second word (or phrase) of each sequence may be compared determine whether such words match, and so on. As illustrated by FIG. 7, performing the method of FIG. 4 on aligned item pair 602 and 610 yields the determination of three misalignments (misalignments 710a, 710b and 710c) and three alignments (alignments 720a, 720b, and 720c). As illustrated, determining a misalignment may include determining that a text string of the first sequence and a corresponding text string of the second sequence do not match (i.e., the text string are not the same). Likewise, determining an alignment may include determining that a text string of the first sequence and a text string of the second sequence do match (i.e., the text string are the same).

As illustrated by block 406, the method may further include assigning a similarity score to the aligned item pair dependent upon the determined misalignments. For example, in one embodiment, for each misalignment detected, the method may include generating a respective subscore for the misalignment. The method may further include generating the similarity score for the aligned item pair by summing each subscore to determine a result and assigning that result to the aligned item pair as the similarity score. In various embodiments, various ones of the subscores may be weighted with corresponding weighting value. In various embodiments, one or more of such weighting values may be configurable.

In various embodiments, the generation of a subscore associated with a misalignment may be dependent upon locating the text strings (e.g., words or phrases) corresponding to the misalignment within a particular corpora of information (e.g., one or more predetermined sets of words or phrases). In various embodiments, such corpora may include one or more variation phrase sets, such as variation phrase sets 176 stored in data store 170, as illustrated in FIG. 1. A variation phrase set may include a stored listing of multiple text strings that are determined to be variants of each other. In some embodiments, a variation phrase set may include a list of colors (e.g., red, blue, yellow, green, magenta, purple, brown, black, etc.). In some embodiments, a variation phrase set may include a list of apparel sizes (e.g., small, medium, large, extra large, S, M, L, XL, XXL, etc.). In some embodiments, a variation phrase set may include a list of hair colors (e.g., blonde, black, brown, red, etc.). The aforesaid examples of variation phrases sets are not meant to be an exhaustive list; in various other embodiments, other variation phrase sets are possible and contemplated.

In various embodiments, the subscore assigned to the misalignment may be positive (or additive). For example, if each of the words (or phrases) of the given misalignment are found within a particular one of the aforesaid predetermined sets of words (e.g., a set of colors, a set of sizes, etc.), the method may include assigning a positive score to the misalignment. In various embodiments, each predetermined set of words or phrases may in some cases be generated from manually-collected (e.g., human-collected) information. For instance, in one embodiment, various data collection and research techniques may be employed to determine specific sets of variant words or phrases. In some embodiments, each predetermined set of words or phrases may be specified as additive (or positive) or subtractive (or negative) (or in some cases, neutral) based on the nature of the predetermined set (e.g., based on the particular words or phrases within the set). For instance, a predetermined set of words that includes words or phrases of a variant set (e.g., a set of color, a set of sizes, etc.) may be specified as a positive predetermined set of words. Likewise, a predetermined set of words that includes words or phrases that have been determined to not be constituents of the same variant set may be specified as a negative predetermined set of words. For instance, in some embodiments, a negative variation phrase set may include a list of compass directions (e.g., north, south, east, west, etc.). In some embodiments, a negative variation phrase set may include a list of sports teams. In some embodiments, a negative variation phrase set may include a list of product names (e.g., pants, shirt, socks, etc.). In some embodiments, a negative variation phrase set may include a list of brand names. The aforesaid examples of negative variation phrases sets are not meant to be an exhaustive list; in various other embodiments, other negative variation phrase sets are possible and contemplated.

In various embodiments, the method may include, for a given misalignment, determining whether each of the text strings associated with the misalignment (e.g., "blue" and "red" of misalignment 710a) are present with the same variation phrase set. For instance, the method may include searching multiple different variation phrase sets (which may include one or more sets of predetermined words, as described above) to determine whether both text strings of the misalignment are stored as members of one of the variation phrase sets. If both text strings, are determined to be present within a particular variation phrase set, the method may include assigning a subscore to the misalignment dependent upon in which variation phrase set the text strings were found. For example misalignment 710a, the method may include searching one or more variation phrase sets for the text strings "blue" and "red." In one example, such text strings may be found within a variation phrase set that comprises a listing of various colors, including both blue and red. In various embodiments, determining that both text strings are present within a particular variation phrase set may increase the probability that the two items corresponding to the aligned item pair are variants of each other (e.g., items that vary by only one or more variant attributes, such as size or color). Accordingly, in such cases, the method may include assigning a positive subscore to the corresponding misalignment.

In some embodiments, determining that both text strings are present within a particular variation phrase set may decrease the probability that the two items corresponding to the aligned item pair are variants of each other. Accordingly, in such cases, the method may include assigning a negative subscore to the corresponding misalignment. For example, in one embodiment, a variation phrase set may include product types that are determined not to be variants of each other. For instance, in one embodiment, the text strings corresponding to a misalignment may include "pant" and "halter," as illustrated by misalignment 710c. In one example, the method may include determining that "pant" and "halter" are both present with a variation phrase set corresponding to different product types (e.g., a negative predetermined set of words or negative variation phrase set, as described above). For instance, such variation phrase set might include the text strings "halter, socks, jeans, pant, shirt, belt, tie, jacket" and other product types. Since "pant" and "halter" are both present within the particular variation phrase set, the method may include assigning a negative subscore to the misalignment. As demonstrated above, some variation phrase sets may be associated with positive subscores, some variation phrase sets may be associated with negative subscores (and some may be associated with neutral or zero-magnitude scores), and the subscore assigned to a given misalignment may be dependent upon the type of subscore (e.g., positive, negative, large, small, etc.) associated with a particular variation phrase set.

In various embodiments, the method may include assigning to an item pair a subscore that is dependent on the length of a misalignment (e.g., the number of text strings of the misalignment) with respect to the length of the sequences of text strings of the item pair (e.g., the number of text strings in the sequence). For instance, in one embodiments, such subscore may be dependent on a ratio of the length of the misalignment to the length of the text sequences of the aligned item pair. In some embodiments, if such ratio is below a threshold, the generated subscore may be punitive (e.g., a negative value). If such ratio is above a threshold, the generated subscore may be additive (e.g., a positive value).

In various embodiments, the method may include determining that a mismatch of two phrases is not to be considered a mismatch. For example, the method may include performing a word-wise analysis on each phrase, and if the two phrases are equivalent on a word level, the method may not consider the two phrases to be a mismatch. For instance, consider the phrases "brown leather" and "leather, brown." In some embodiments, the method may include determining that each phrase includes the same words and are thus equivalent.

In some embodiments, when evaluating two sequences of text strings for an aligned item pair, the method may include determining that a given text strings of one sequence does not have a corresponding text string in the other sequence. For instance, such situation might arise when one sequence of text strings is longer than the other; the remaining text string(s) of the longer sequence may not have corresponding text string (s) in the other sequence. In some embodiments, the method may include determining that a remaining text string is a natural language word. For instance, the method may include determining a text string to one or more entries within a dictionary of natural language words (e.g., a dictionary stored in data store 170). Furthermore, in some embodiments, the method may include determining that natural language words are to be considered noise and that such words are to be ignored with respect to the calculation of the similarity score of the aligned item pair. In other embodiments, the method may include determining that a remaining text string is an item identifier (e.g., a stock keeping unit or model number) and assigning a corresponding subscore to the aligned text pair. For instance, the method may include comparing the text strings to records of item identifiers to determine whether the text strings is present in such records.

In various embodiments, each predetermined set of words (which is also referred to herein as a variation phrases set) may be stored within a repository or knowledge base that includes multiple ones of such sets. As described above, various ones of the predetermined sets of words or phrases may be used to assign subscores to various misalignments. In various embodiments, the knowledge base that includes such sets of words may be iteratively updated as new information is determined (e.g., manually determined by a human). For instance, in one embodiment, a new color or size may be determined and added to a respective predetermined set of words or phrases.

Figure 5:
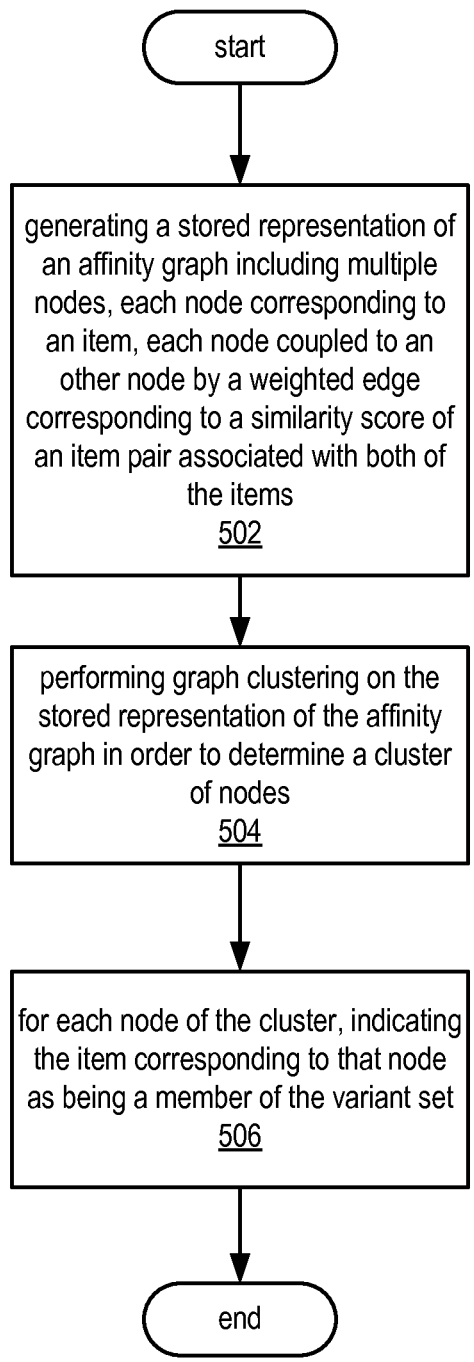
FIG. 5 illustrates a flowchart of an example method for performing graph clustering to determine a variant set of items, according to some embodiments.
Figure 8:
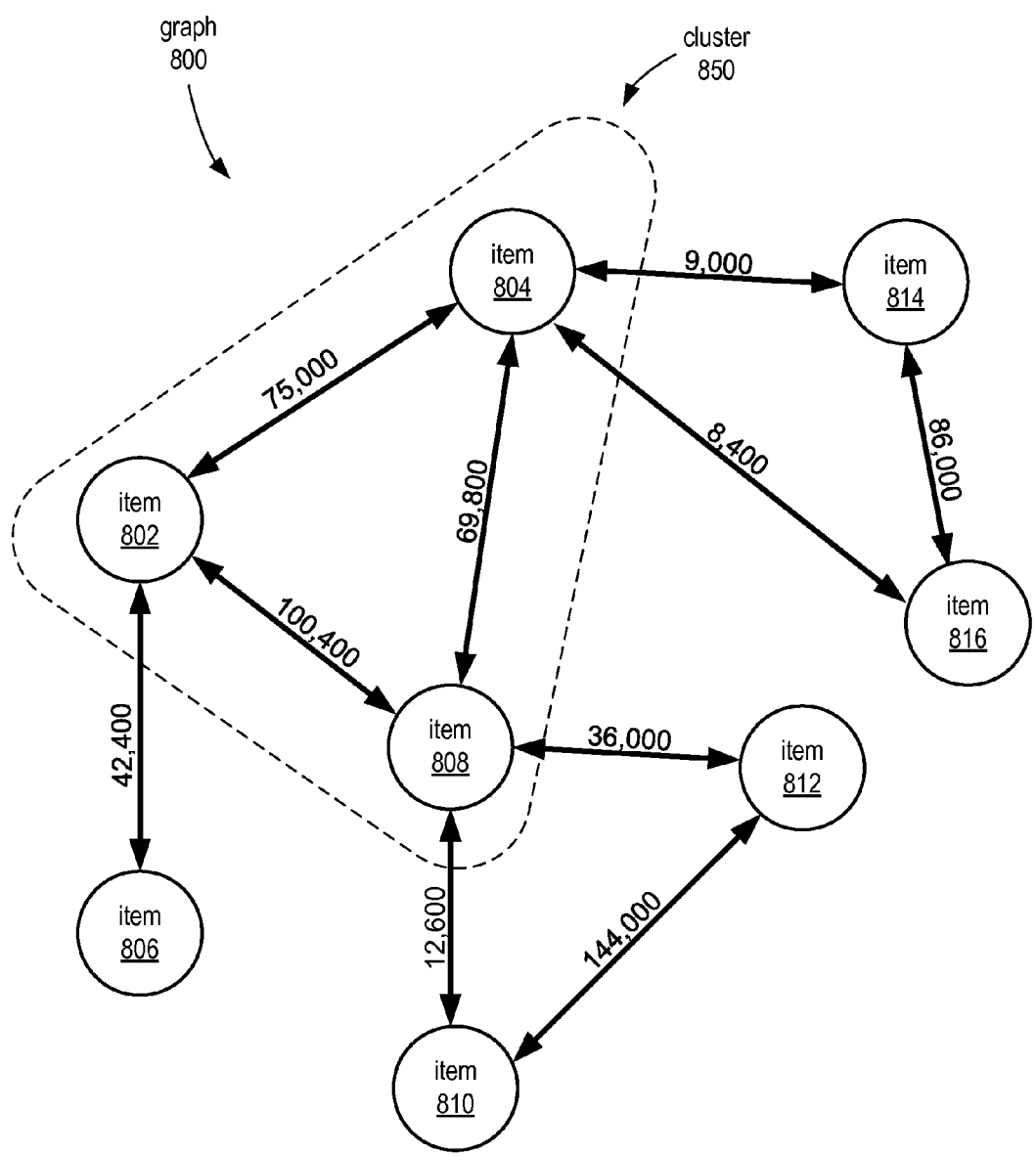
FIG. 8 illustrates one example of an affinity graph on which graph clustering techniques may be performed, according to some embodiments.

FIG. 5 illustrates a flowchart of one example for determining a variant set of items (e.g., a set of items that only differ by one or more variant attributes). In various embodiments, the illustrated method may be performed by the variant detection component described above. As illustrated by block 502, the method may include generating a stored representation of an affinity graph that includes multiple nodes with weighted couplings or "edges" between each node. (Note that in some cases, one or more nodes of an affinity graph may not be connected to any other node; such nodes may be referred to as "singletons"). In various embodiments, a node of the graph may be generated for each item, and a weighted edge between two nodes may correspond to a similarity score (e.g., the similarity scores described above, such as a summation of subscores as described above) generated for the aligned item pair that include the two items to which the two nodes correspond. Referring collectively to FIG. 5 and FIG. 8, one example of an affinity graph 800 is illustrated. Each of items 802-826 may be a node within the affinity graph. Additionally, the presence of a weighted (or scored) edge between two nodes of the graph indicates that the two items corresponding to those nodes are members of an aligned item pair. In some embodiments, some nodes of the graph may be removed if they are not coupled to another node by an edge meeting a threshold score. For instance, if a threshold of 9,000 were applied to the illustrated graph, the edge between item 816 and item 804 would be removed (since the score of that edge is 8400, which is less than 9,000).

As illustrated by block 504, the method may include performing graph clustering on the stored representation of the affinity graph in order to determine a cluster of nodes, such as cluster 850 (which corresponds to a cluster of items). In various embodiments, performing graph clustering on the stored representation may include performing a graph clustering algorithm or technique on the stored representation of the affinity graph, whether such algorithms or techniques are presently known or developed in the future. In one particular embodiment, the method may include performing a parallel graph clustering algorithm to determine a one or more clusters of nodes. In some embodiments, the method may include utilizing the Markov Clustering (MCL) technique to determine one or more clusters of nodes. In some embodiments, the method may include performing a recursive graph clustering algorithm or technique in order to partition an affinity graph into subgraphs and eventually into clusters of nodes. In some embodiments, such a recursive technique may be controlled by a threshold for the mean distance between nodes of the affinity graph. In various embodiments, clusters may be determined in an iterative fashion. For example, in some embodiments, the method described herein may include generating an affinity graph and, as additional item data is received for a particular item, appending a node for that item to a its most closely related (e.g., as based on similarity scores) cluster. Such process may be repeated for subsequent items. By performing such process in an iterative fashion, the method may in some embodiments conserve computing resources, as the method does not require an entire affinity be regenerated every time new item data is received from a merchant. Note that while only one cluster is presented in the illustrated example, the method may include determining any number of clusters within an affinity graph.

As illustrated by block 506, the method may include, for each node of the cluster, indicating the item corresponding to that node as being a member of a variant set. For instance, in the illustrated example, the method may include indicating that items 802, 804, and 808 are each members of the same variant set of items (e.g., a set of items that only varies by one or more variant attributes, as described above). In one embodiment, indicating items (corresponding to respective nodes of a cluster) as members of a variant set may include generating a stored data structure for the variant set, the stored data structure including identifiers for the items. In various embodiments, some clusters may include only one node (e.g., a singleton); a variant set corresponding to such a cluster may include only one item.

As described above, each variant set determined may be utilized for a variety of purposes. In one embodiment, a variant set may be utilized to consolidate search results by presenting only a single search result for a given variant set (e.g., a "parent" search result). The other search results of that variant set (e.g., "child" search results) may be hidden from view in the list of search results. In other cases, multiple product detail pages may be collapsed into a single product detail page (e.g., for a "parent" item) from which one or more variant attributes may be selected in order to select a particular item of the variant set (a "child" item).

Example System

Various embodiments of a method and system for determining sets of variant items, as described herein, may be executed on one or more computer systems, which may interact with various other devices. One such computer system is computer system 900 illustrated by FIG. 9, which in the illustrated example may implement host system 110. Computer system 900 may be capable of implementing a variant detection component, such as variant detection component 100. In the illustrated embodiment, computer system 900 includes one or more processors 910 coupled to a system memory 920 via an input/output (I/O) interface 930. Computer system 900 further includes a network interface 940 coupled to I/O interface 930, and one or more input/output devices 950, such as cursor control device 960, keyboard 970, and display(s) 980. In some embodiments, it is contemplated that embodiments may be implemented using a single instance of computer system 900, while in other embodiments multiple such systems, or multiple nodes making up computer system 900, may be configured to host different portions or instances of embodiments. For example, in one embodiment some elements may be implemented via one or more nodes of computer system 900 that are distinct from those nodes implementing other elements.

In various embodiments, computer system 900 may be a uniprocessor system including one processor 910, or a multiprocessor system including several processors 910 (e.g., two, four, eight, or another suitable number). Processors 910 may be any suitable processor capable of executing instructions. For example, in various embodiments processors 910 may be general-purpose or embedded processors implementing any of a variety of instruction set architectures (ISAs), such as the x86, PowerPC, SPARC, or MIPS ISAs, or any other suitable ISA. In multiprocessor systems, each of processors 910 may commonly, but not necessarily, implement the same ISA.

System memory 920 may be configured to store program instructions 922 and/or data 932 accessible by processor 910. In various embodiments, system memory 920 may be implemented using any suitable memory technology, such as static random access memory (SRAM), synchronous dynamic RAM (SDRAM), nonvolatile/Flash-type memory, or any other type of memory. In the illustrated embodiment, program instructions and data implementing variant detection component, such as variant detection component 100 described above, are shown stored within system memory 920 as variation detection component 100. In other embodiments, program instructions and/or data may be received, sent or stored upon different types of computer-accessible media or on similar media separate from system memory 920 or computer system 900. Generally speaking, a computer-accessible medium may include storage media or memory media such as magnetic or optical media, e.g., disk or CD/DVD-ROM coupled to computer system 900 via I/O interface 930. Program instructions and data stored via a computer-accessible medium may be transmitted by transmission media or signals such as electrical, electromagnetic, or digital signals, which may be conveyed via a communication medium such as a network and/or a wireless link, such as may be implemented via network interface 940.

In one embodiment, I/O interface 930 may be configured to coordinate I/O traffic between processor 910, system memory 920, and any peripheral devices in the device, including network interface 940 or other peripheral interfaces, such as input/output devices 950. In some embodiments, I/O interface 930 may perform any necessary protocol, timing or other data transformations to convert data signals from one component (e.g., system memory 920) into a format suitable for use by another component (e.g., processor 910). In some embodiments, I/O interface 930 may include support for devices attached through various types of peripheral buses, such as a variant of the Peripheral Component Interconnect (PCI) bus standard or the Universal Serial Bus (USB) standard, for example. In some embodiments, the function of I/O interface 930 may be split into two or more separate components, such as a north bridge and a south bridge, for example. Also, in some embodiments some or all of the functionality of I/O interface 930, such as an interface to system memory 920, may be incorporated directly into processor 910.

Network interface 940 may be configured to allow data to be exchanged between computer system 900 and other devices attached to a network (e.g., network 180), such as other computer systems (e.g., merchant system 130), or between nodes of computer system 900. In various embodiments, network interface 940 may support communication via wired or wireless general data networks, such as any suitable type of Ethernet network, for example; via telecommunications/telephony networks such as analog voice networks or digital fiber communications networks; via storage area networks such as Fibre Channel SANs, or via any other suitable type of network and/or protocol.

Input/output devices 950 may, in some embodiments, include one or more display terminals, keyboards, keypads, touchpads, scanning devices, voice or optical recognition devices, or any other devices suitable for entering or accessing data by one or more computer systems 900. Multiple input/output devices 950 may be present in computer system 900 or may be distributed on various nodes of computer system 900. In some embodiments, similar input/output devices may be separate from computer system 900 and may interact with one or more nodes of computer system 900 through a wired or wireless connection, such as over network interface 940.

Figure 9:
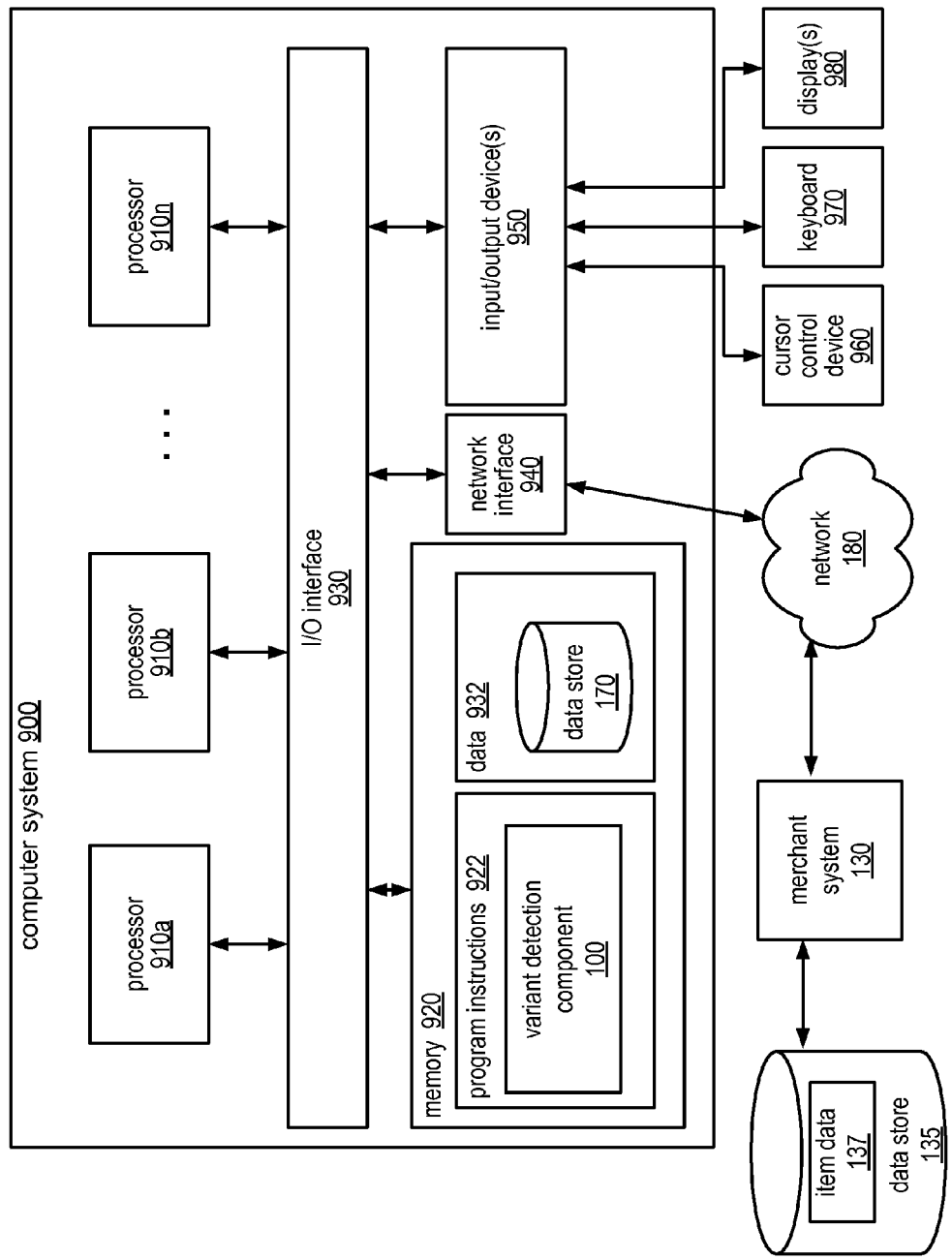
FIG. 9 illustrates one example of a system for implementing a variant detection component, according to some embodiments.

As shown in FIG. 9, memory 920 may include program instructions 922 configured to implement a variant detection component, such as variant detection component 100. In one embodiment, variant detection component 100 may implement the methods described above, such as the methods illustrated by FIGS. 2-5. In other embodiments, different elements and data may be included. As illustrated, note that data 932 may include the contents of data store 170. In other embodiments, data store 170 may be external to and coupled to computer system 900.

Those skilled in the art will appreciate that computer system 900 is merely illustrative and is not intended to limit the scope of embodiments. In particular, the computer system and devices may include any combination of hardware or software that can perform the indicated functions, including computers, network devices, Internet appliances, PDAs, wireless phones, pagers, etc. Computer system 900 may also be connected to other devices that are not illustrated, or instead may operate as a stand-alone system. In addition, the functionality provided by the illustrated components may in some embodiments be combined in fewer components or distributed in additional components. Similarly, in some embodiments, the functionality of some of the illustrated components may not be provided and/or other additional functionality may be available.

Those skilled in the art will also appreciate that, while various items are illustrated as being stored in memory or on storage while being used, these items or portions of them may be transferred between memory and other storage devices for purposes of memory management and data integrity. Alternatively, in other embodiments some or all of the software components may execute in memory on another device and communicate with the illustrated computer system via inter-computer communication. Some or all of the system components or data structures may also be stored (e.g., as instructions or structured data) on a computer-accessible medium or a portable article to be read by an appropriate drive, various examples of which are described above. In some embodiments, instructions stored on a computer-accessible medium separate from computer system 900 may be transmitted to computer system 900 via transmission media or signals such as electrical, electromagnetic, or digital signals, conveyed via a communication medium such as a network and/or a wireless link. Various embodiments may further include receiving, sending or storing instructions and/or data implemented in accordance with the foregoing description upon a computer-accessible medium. Accordingly, various embodiments may be practiced with other computer system configurations.

Various embodiments may further include receiving, sending or storing instructions and/or data implemented in accordance with the foregoing description upon a computer-accessible medium. Generally speaking, a computer-accessible medium may include storage media or memory media such as magnetic or optical media, e.g., disk or DVD/CD-ROM, volatile or non-volatile media such as RAM (e.g. SDRAM, DDR, RDRAM, SRAM, etc.), ROM, etc. Computer-accessible memory may also include transmission media or signals such as electrical, electromagnetic, or digital signals, conveyed via a communication medium such as network and/or a wireless link.

The methods described herein may be implemented in software, hardware, or a combination thereof, in different embodiments. In addition, the order of the blocks of the methods may be changed, and various elements may be added, reordered, combined, omitted, modified, etc. Various modifications and changes may be made as would be obvious to a person skilled in the art having the benefit of this disclosure. The various embodiments described herein are meant to be illustrative and not limiting. Many variations, modifications, additions, and improvements are possible. Accordingly, plural instances may be provided for components described herein as a single instance. Boundaries between various components, operations and data stores are somewhat arbitrary, and particular operations are illustrated in the context of specific illustrative configurations. Other allocations of functionality are envisioned and may fall within the scope of claims that follow. Finally, structures and functionality presented as discrete components in the exemplary configurations may be implemented as a combined structure or component. These and other variations, modifications, additions, and improvements may fall within the scope of embodiments as defined in the claims that follow.

What is claimed is:

1. A computer-implemented method, comprising:
    performing, by one or more computers having at least one processor and memory:
        accessing data that includes, for each individual item of individual ones of a plurality of items, a corresponding one or more text strings that describe, and are distinct from, the individual item;
        for each particular item of at least some of the individual ones of the plurality of items:
            for each of one or more other items of the individual ones of the plurality of items that are distinct from the particular item, comparing the one or more text strings describing the other item with the one or more text strings describing the particular item;
            based at least in part on said comparing, identifying at least one of the one or more other items that are each distinct from, but a potential variant of, the particular item;
            subsequent to said identifying, and for each identified other item of at least some of the one or more identified other items, generating an aligned pair, wherein one member of the aligned pair comprises the one or more text strings describing the identified other item, and the other member of the aligned pair comprises the one or more text strings describing the particular item, and wherein said generating comprises aligning the text in the one member with respect to the text in the other member; and
            subsequent to said generating, and for each aligned pair of at least some of the one or more aligned pairs:
                determining one or more misalignments between the text in one member of the aligned pair and the text in the other member of the aligned pair; and
                assigning a similarity score to the aligned pair, wherein the similarity score depends at least in part on the determined one or more misalignments, and indicates a degree of confidence that the particular item that corresponds to the one or more text strings of one member of the aligned pair, and the other item that corresponds to the one or more text strings of the other member of the aligned pair, are distinct variants of each other;
        based at least in part on a plurality of the generated aligned pairs, and on the similarity scores assigned to each of those aligned pairs, determining one or more variant sets of items from the plurality of items, wherein each variant set comprises multiple items of the plurality of items such that each item of the variant set is indicated to be a variant of a same item;
        generating a network-based page based at least in part on the determined one or more variant sets of items; and
        transmitting the generated network-based page over a communication network to a client computing device.

2. The computer-implemented method of claim 1, wherein said determining the one or more variant sets comprises:
    generating a stored representation of an affinity graph comprising multiple nodes, wherein each node corresponds to one item of the plurality of items and is coupled to at least one other node of the multiple nodes by a weighted edge to which an item similarity weight is assigned;
    wherein the item similarity weight assigned to each weighted edge that couples a first node and a second node of the multiple nodes is based, at least in part, on the similarity score assigned to an aligned pair of the generated aligned pairs whose first member comprises one or more text strings describing the item corresponding to the first node, and whose second member comprises one or more text strings describing the item corresponding to the second node;
    performing graph clustering on the stored representation of the affinity graph to determine one or more clusters of nodes, wherein said graph clustering determines which nodes to include in a cluster based, at least in part, on the item similarity weights assigned to the weighted edges coupling the nodes of the affinity graph which are to be included in cluster; and for each cluster of at least some of the determined one or more clusters, indicating that the items corresponding to the nodes in the cluster belong to a same variant set of the one or more variant sets.

3. The computer-implemented method of claim 1, wherein said corresponding one or more text strings that describe, and are distinct from, the individual item to which they correspond comprise one or more of: a title for the individual item, variant attributes of the individual item, a product description of the individual item, and specifications of the individual item.

4. The computer-implemented method of claim 1, further comprising receiving said corresponding one or more text strings that describe, and are distinct from, the individual item to which they correspond from a merchant supplying the individual item.

5. The computer-implemented method of claim 1, wherein the data include an index of the plurality of items, and said accessing and said comparing include searching the index in order to identify the at least one of the one or more other items that are each distinct from, but a potential variant of, the particular item.

6. The computer-implemented method of claim 1, wherein said aligning the text in the one member with respect to the text in the other member comprises applying a text alignment algorithm to align the one or more text strings of the one member with respect to the one or more text strings of the other member.

7. The computer-implemented method of claim 6, wherein the text alignment algorithm comprises a version of a Needleman-Wunsch algorithm for aligning a group of one or more text strings with another group of one or more text strings.

8. The computer-implemented method of claim 7, wherein the version of the Needleman-Wunsch algorithm is weighted such that when performing said aligning the text in the one member with respect to the text in the other member, said applying the version of the Needleman-Wunsch algorithm penalizes a gap detected in the one or more text strings of the one member or the one or more text strings of the other member more than it penalizes a mismatch between the one or more text strings of the one member and the one or more text strings of the other member.

9. The computer-implemented method of claim 1, wherein the determined one or more misalignments comprise multiple misalignments;

wherein the method further includes, for each individual misalignment of the multiple misalignments, determining a respective subscore for the aligned pair based on the individual misalignment; and wherein said assigning the similarity score to the aligned pair comprises assigning a result of a summation of the multiple subscores assigned to the aligned pair.

10. A system, comprising:

a memory comprising program instructions; and one or more processors coupled to said memory, wherein the program instructions are executable by at least one of said one or more processors to perform:

accessing data that includes, for each individual item of individual ones of a plurality of items, a corresponding one or more text strings that describe, and are distinct from, the individual item;

for each particular item of at least some of the individual ones of the plurality of items:

for each of one or more other items of the individual ones of the plurality of items that are distinct from the particular item, comparing the one or more text strings describing the other item with the one or more text strings describing the particular item;

based at least in part on said comparing, identifying at least one of the one or more other items that are each distinct from, but a potential variant of, the particular item;

subsequent to said identifying, and for each identified other item of at least some of the one or more identified other items, generating an aligned pair, wherein one member of the aligned pair comprises the one or more text strings describing the identified other item, and the other member of the aligned pair comprises the one or more text strings describing the particular item, and wherein said generating comprises aligning the text in the one member with respect to the text in the other member; and subsequent to said generating, and for each aligned pair of at least some of the one or more aligned pairs:

determining one or more misalignments between the text in one member of the aligned pair and the text in the other member of the aligned pair; and assigning a similarity score to the aligned pair, wherein the similarity score depends at least in part on the determined one or more misalignments, and indicates a degree of confidence that the particular item that corresponds to the one or more text strings of one member of the aligned pair, and the other item that corresponds to the one or more text strings of the other member of the aligned pair, are distinct variants of each other;

based at least in part on a plurality of the generated aligned pairs, and on the similarity scores assigned to each of those aligned pairs, determining one or more variant sets of items from the plurality of items, wherein each variant set comprises multiple items of the plurality of items such that each item of the variant set is indicated to be a variant of a same item generating a network-based page based at least in part on the determined one or more variant sets of items; and transmitting the generated network-based page over a communication network to a client computing device.

11. The system of claim 10, wherein to perform said determining the one or more variant sets, the program instructions are further configured to perform:

generating a stored representation of an affinity graph comprising multiple nodes, wherein each node corresponds to one item of the plurality of items and is coupled to at least one other node of the multiple nodes by a weighted edge to which an item similarity weight is assigned;

wherein the item similarity weight assigned to each weighted edge that couples a first node and a second node of the multiple nodes is based, at least in part, on the similarity score assigned to an aligned pair of the generated aligned pairs whose first member comprises one or more text strings describing the item corresponding to the first node, and whose second member comprises one or more text strings describing the item corresponding to the second node;

performing graph clustering on the stored representation of the affinity graph to determine one or more clusters of nodes, wherein said graph clustering determines which nodes to include in a cluster based, at least in part, on the item similarity weights assigned to the weighted edges coupling the nodes of the affinity graph which are to be included in cluster; and for each cluster of at least some of the determined one or more clusters, indicating that the items corresponding to the nodes in the cluster belong to a same variant set of the one or more variant sets.

12. The system of claim 10, wherein said corresponding one or more text strings that describe, and are distinct from, the individual item to which they correspond comprise one or more of: a title for the individual item, variant attributes of the individual item, a product description of the individual item, and specifications of the individual item.

13. The system of claim 10, wherein to perform said determining the one or more misalignments, the program instructions are further configured to perform, for at least one misalignment of the determined one or more misalignments between the text in one member of the aligned pair and the text in the other member of the aligned pair, determining that a word of the text in one member of the aligned pair does not match a corresponding other word of the text in the other member of the aligned pair.

14. The system of claim 13, wherein the program instructions are further configured to, for the at least one misalignment of the determined one or more misalignments, assign a subscore to the aligned pair based on determining that the word and the corresponding other word match words of a predetermined set of words.

15. The system of claim 14, wherein the predetermined set of words comprises one or more of: a set of multiple colors, a set of multiple sizes, a set of multiple product names, a set of multiple brands, and a set of multiple sports teams.

16. A computer-readable non-transitory storage medium storing program instructions computer-executable to perform:

accessing data that includes, for each individual item of individual ones of a plurality of items, a corresponding one or more text strings that describe, and are distinct from, the individual item;

for each particular item of at least some of the individual ones of the plurality of items:

for each of one or more other items of the individual ones of the plurality of items that are distinct from the particular item, comparing the one or more text strings describing the other item with the one or more text strings describing the particular item;

based at least in part on said comparing, identifying at least one of the one or more other items that are each distinct from, but a potential variant of, the particular item;

subsequent to said identifying, and for each identified other item of at least some of the one or more identified other items, generating an aligned pair, wherein one member of the aligned pair comprises the one or more text strings describing the identified other item, and the other member of the aligned pair comprises the one or more text strings describing the particular item, and wherein said generating comprises aligning the text in the one member with respect to the text in the other member; and subsequent to said generating, and for each aligned pair of at least some of the one or more aligned pairs:

determining one or more misalignments between the text in one member of the aligned pair and the text in the other member of the aligned pair; and assigning a similarity score to the aligned pair, wherein the similarity score depends at least in part on the determined one or more misalignments, and indicates a degree of confidence that the particular item that corresponds to the one or more text strings of one member of the aligned pair, and the other item that corresponds to the one or more text strings of the other member of the aligned pair, are distinct variants of each other;

based at least in part on a plurality of the generated aligned pairs, and on the similarity scores assigned to each of those aligned pairs, determining one or more variant sets of items from the plurality of items, wherein each variant set comprises multiple items of the plurality of items such that each item of the variant set is indicated to be a variant of a same item generating a network-based page based at least in part on the determined one or more variant sets of items; and transmitting the generated network-based page over a communication network to a client computing device.

17. The computer-readable non-transitory storage medium of claim 16, wherein to perform said determining the one or more variant sets, the program instructions are further computer-executable to perform:

generating a stored representation of an affinity graph comprising multiple nodes, wherein each node corresponds to one item of the plurality of items and is coupled to at least one other node of the multiple nodes by a weighted edge to which an item similarity weight is assigned;

wherein the item similarity weight assigned to each weighted edge that couples a first node and a second node of the multiple nodes is based, at least in part, on the similarity score assigned to an aligned pair of the generated aligned pairs whose first member comprises one or more text strings describing the item corresponding to the first node, and whose second member comprises one or more text strings describing the item corresponding to the second node;

performing graph clustering on the stored representation of the affinity graph to determine one or more clusters of nodes, wherein said graph clustering determines which nodes to include in a cluster based, at least in part, on the item similarity weights assigned to the weighted edges coupling the nodes of the affinity graph which are to be included in cluster; and for each cluster of at least some of the determined one or more clusters, indicating that the items corresponding to the nodes in the cluster belong to a same variant set of the one or more variant sets.

18. The computer-readable non-transitory storage medium of claim 16, wherein said corresponding one or more text strings that describe, and are distinct from, the individual item to which they correspond comprise one or more of: a title for the individual item, variant attributes of the individual item, a product description of the individual item, and specifications of the individual item.

19. The computer-readable non-transitory storage medium of claim 16, wherein the program instructions are further computer-executable to perform receiving said corresponding one or more text strings that describe, and are distinct from, the individual item to which they correspond from a merchant supplying the individual item.

20. The computer-readable non-transitory storage medium of claim 16, wherein the determined one or more misalignments of the aligned pair comprise multiple misalignments; wherein the program instructions are further computer-executable to perform, for each individual misalignment of the multiple misalignments, determining a respective subscore for the aligned pair based on the individual misalignment; and wherein said assigning the similarity score to the aligned pair comprises assigning a result of a summation of the multiple subscores assigned to the aligned pair.

* * * * *